United States Patent [19]

Sunkara et al.

[11] Patent Number: 5,182,293
[45] Date of Patent: Jan. 26, 1993

[54] TREATMENT OF MULTI-DRUG RESISTANT TUMORS WITH PYRIDYLOXAZOLE-2-ONES

[75] Inventors: Sai P. Sunkara; Winton D. Jones, both of Cincinnati, Ohio

[73] Assignee: Merrell Dow Pharmaceuticals Inc., Cincinnati, Ohio

[21] Appl. No.: 590,524

[22] Filed: Oct. 3, 1990

Related U.S. Application Data

[63] Continuation-in-part of Ser. No. 436,263, Nov. 13, 1989, abandoned.

[51] Int. Cl.⁵ .............................................. A61K 31/44
[52] U.S. Cl. ...................................... 514/340; 424/10
[58] Field of Search ........................... 514/340; 424/10

[56] References Cited

U.S. PATENT DOCUMENTS 4,698,353  10/1987  Schnettler et al. ................. 514/340
4,886,811  12/1989  Jones et al. ......................... 514/314

Primary Examiner—Jerome D. Goldberg
Attorney, Agent, or Firm—Stephen L. Nesbitt

[57] ABSTRACT

This invention relates to pyridinyloxazole-2-ones which are useful in the treatment of multi-drug resistant tumors. The pyridinyloxazole-2-ones act to prevent drug resistance and thus allow conventional chemotherapeutic agents to kill tumor cells as if drug resistance were not present.

1 Claim, No Drawings

TREATMENT OF MULTI-DRUG RESISTANT TUMORS WITH PYRIDYLOXAZOLE-2-ONES

This is a continuation-in-part of application Ser. No. 07/436,263, filed Nov. 13, 1989, now abandoned.

This invention relates to the use of certain pyridinyloxazole-2-ones in the treatment of multi-drug resistant tumors.

BACKGROUND OF THE INVENTION

Effective tumor treatment is frequently thwarted by the lack of sensitivity of certain tumors to standard chemotherapeutic agents (intrinsic resistance) or by the ability of certain tumors to develop a lack of chemotherapeutic sensitivity during the course of treatment (acquired resistance). The cause of this phenomena has, at least in part, been demonstrated to result from the existance of an energy-dependent efflux pump which acts to remove the chemotherapeutic agent from the target cell.

The pump consists of P-glycoprotein found as a constitutent of cell membrane, and it has been suggested that the normal function of P-glycoprotein is to remove toxins from within the cell. This theory is supported by the observation that P-glycoprotein is found as a cell membrane constituent in cells such as liver, kidney, colon, and jejunum. It has been suggested that P-glycoprotein in the cell membrane of such normal tissues could act to remove toxins or to assist in the transport of nutrients and solutes and in secreting a variety of protein and steroid substances. Natural presence of P-glycoprotein in tumor cells derived from these tissues as well as its presence in tumor cells derived from other tissue types could explain, at least in part, resistance of various tumors to therapy with standard chemotheraputic agents.

The use of therapeutic agents which inactivate the P-glycoprotein pump would be invaluable in the treatment of multidrug-resistant tumors. Quinidine and reserpine as well as the calcium channel blockers verapamil and diltiazem have been reported to reverse drug resistance in multidrug-resistant tumors. Such agents could function by, for example, interfering with transcription of the P-glycoprotein gene, blocking the drug binding site on the P-glycoprotein or by decoupling the energy dependent driving mechanism of the efflux pump.

Applicants have determined that certain pyridinyloxazole-2-ones having PKC inhibiting activity are useful in the treatment of multi-drug resistant tumors. The pyridinyloxazolone-2-ones of this invention act to reverse drug resistance and thereby allow standard chemotherapeutic agents to exhibit normal toxicity on tumors.

SUMMARY OF THE INVENTION

The present invention is directed to the use of certain pyridinyloxazole-2-ones of the formula

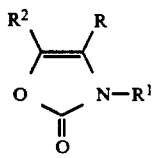

(I)

wherein
R and $R^1$ are each independently selected from the group consisting of hydrogen, $C_1$-$C_6$ alkyl, and phenyl or $C_1$-$C_3$ alkylphenyl wherein the phenyl ring is optionally substituted with one, two or three of the substituents selected from the group consisting of fluorine, chlorine, bromine, $C_1$-$C_4$ alkyl, and $C_1$-$C_4$ alkoxy; and $R^2$ is a 2-, 3-, or 4-pyridyl group wherein the pyridyl group is optionally substituted with one or two substituents selected from the group consisting of fluorine, chlorine, bromine, $C_1$-$C_4$ alkyl, $C_{1-4}$ alkoxy, $C_1$-$C_4$ alkylthio, $C_1$-$C_4$ alkylsulfinyl, $C_1$14 $C_4$ alkylsulfonyl, cyano, carboxy, carb($C_1$-$C_5$)alkoxy, carbamido, ($C_1$-$C_5$)alkanoylamino, imidazolyl, nitro and trifluoromethyl or wherein the pyridyl group is optionally substituted with a phenyl group which is optionally substituted with one, two or three of the substituents selected from the group consisting of fluorine, chlorine, bromine, $C_1$-$C_4$ alkyl, and $C_1$-$C_4$ alkoxy;

and the pharmaceutically-acceptable salts thereof in the treatment of multidrug-resistant tumors.

DETAILED DESCRIPTION OF THE INVENTION

This invention concerns the use of the compounds of Formula I as agents effective in the treatment of multi-drug resistant tumors. Specifically the compounds of formula I, when administered together with standard chemotherapeutic agents, can be used in the treatment of tumors which are intrinsically or extrinsically drug resistant.

As used herein, the terms "$C_1$-$C_3$ alkyl", "$C_1$-$C_4$ alkyl" and "$C_1$ -$C_6$ alkyl38 mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propynyl, butenyl, butadienyl, isopropenyl, and the like. The term "$C_1$-$C_4$ alkoxy" means alkoxy groups having from one to four carbon atoms, and includes such groups as methoxy, ethoxy, n-propyoxy, propoxy, isopropoxy, n-butoxy, isobutoxy, sec-butoxy, tert-butoxy, and the like. When R or $R^1$ is "optionally substituted phenyl or $C_1$-$C_3$ alkylphenyl", the one, two or three substituent(s) can be located at any available position on the phenyl ring.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are,for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of this invention include compounds of Formula I wherein the R groups are designated as follows:

| R | $R^1$ | $R^2$ |
|---|---|---|
| hydrogen | hydrogen | 2-, 3-, or 4-pyridinyl |
| ethyl | hydrogen | 2-, 3-, or 4-pyridinyl |
| propyl | hydrogen | 5-, 6-, 7- or 8-pyridinyl |
| methyl | benzyl | 2-, 3- or 4-pyridinyl |
| phenethyl | hydrogen | 2-, 3- or 4-pyridinyl |
| phenyl | hydrogen | 2-, 3- or 4-pyridinyl |
| propyl | hydrogen | 2-, 3- or 4-(6,7-dimethyl)-pyridinyl |
| propyl | hydrogen | 2-, 3-, or 4-(6-phenyl)-pyridinyl |
| 4-methoxyphenethyl | hydrogen | 2, 3- or 4-pyridinyl |
| 4-methoxyphenyl | hydrogen | 2, 3- or 4-pyridinyl |
| benzyl | benzyl | 2-, 3- or 4-(7-ethoxy)-pyridinyl |
| phenyl | phenyl | 2-, 3- or 4-(7-ethoxy)-pyridinyl |
| phenyl | phenyl | 2-, 3-, or 4-(7-phenyl)-pyridinyl |
| butyl | hydrogen | 2-, 3- or 4-pyridinyl |
| 3,5-dichloro-phenylpropyl | methyl | 5-, 6-, 7- or 8-pyridinyl |
| 3,5-dichloro)phenyl | methyl | 5-, 6-, 7- or 8-pyridinyl |
| propyl | methyl | 2-, 3- or 4-pyridinyl |
| 3,5-dimethoxybenzyl | ethyl | 5-, 6-, 7- or 8-pyridinyl |
| 3,5-dimethoxyphenyl | ethyl | 5-, 6-, 7- or 8-pyridinyl |
| methyl | propyl | 2-, 3- or 4-(5-ethoxy-7-methyl)-pyridinyl |
| butyl | butyl | 5-, 6-, 7- or 8-pyridinyl |
| hydrogen | phenethyl | 2-, 3- or 4-(6-trifluoromethyl)-pyridinyl |
| hydrogen | phenethyl | 2-, 3-, or 4-(6-phenyl)-pyridinyl |
| methyl | 4-methoxy-phenethyl | 2-, 3- or 4-pyridinyl |

As is true for most classes of therapeutically effective compounds, certain subclasses and certain species are especially effective and are preferred over others. In this instance, those compounds of Formula I wherein $R^2$ is optionally substituted 2-, 3-, or 4-pyridinyl are preferred. Also preferred are compounds wherein R is hydrogen or a $C_1$–$C_6$ alkyl. Most preferred are the compounds wherein R2 is an unsubstituted 2-, 3-, or 4-pyridinyl group, R is propyl and $R^1$ is hydrogen. The most preferred compound of this invention is 4-propyl-5-(4-pyridinyl)-2(3H)-oxazolone.

The preparation of the 2-, 3-, or 4-pyridinyloxazole-2-ones of this invention is known in the art. See for example, U.S. Pat. No. 4,698,353. The preparation of those compounds not specifically taught in the art can be readily accomplished by the skilled artisan.

In essence, the compounds of this invention can be prepared by reacting a compound of formula 2

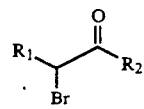

(2)

wherein $R_1$ and $R_2$ are as defined above with a cyanate in DMF to form the corresponding isocyanate which undergoes cyclization under the reaction conditions to yield the desired formula 1 product.

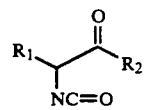

(3)

Another procedure involves cyclizing a hydroxyketone of structure 4

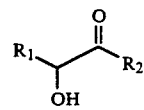

(4)

wherein $R_1$ and $R_2$ are as defined above by reaction with a cyanate or salt in the presence of an acid.

The bromo-ketones of formula 2 are either known in the art or can be readily prepared by standard techniques. For example the des-bromo analog of a structure 2 compound can be treated with bromine. Where the group adjacent to the carbon to be brominated is a hydrogen or a ($C_1$–$C_5$) alkyl group, a radical initiator can be used to promote the bromination. Suitable initiators include iron metal and N-bromosuccinimide. The bromination can also be accomplished by the addition of centrated hydrobromic acid, typically 48% aqueous hydrobromic acid, to a solution containing des-bromo compound. The structure (4) hydroxyketones can also be readily prepared in any suitable manner. For example, a structure 2 bromo-ketone can be allowed to react with an acetate salt, preferably potassium acetate, to form the corresponding acetoxyketone which upon treatment with an acid, such as hydrochloric acid, yields the desired structure (4) compound.

The compounds wherein R is $C_1$–$C_6$ alkyl or optionally substituted phenyl or $C_1$–$C_3$ alkylphenyl are produced by subsequent reaction of the compound of Formula 1 wherein R hydrogen with sodium hydride and the appropriate alkyl iodide or phenylalkyl iodide in tetrahydrofuran according to procedures well known in the art.

The compounds of this invention are useful both in the free base form and as salts. The expression "pharmaceutically-acceptable salt" means any organic or inorganic addition salt of the base compounds of Formula I which are relatively non-toxic and innocuous to a patient at concentrations consistent with effective activity so that the side effects ascribable to the salt do not vitiate the beneficial effects of the base compounds of Formula I. These salts are included within the scope of this invention. Such salts include alkali metal salts, such as sodium and potassium salts and alkaline earth metal salts, such as calcium and magnesium salts; and the like. Also salts with organic and inorganic acids can be prepared, such as, for example, those formed with the following acids: hydrochloric, hydrobromic, sulfonic, sulfuric, phosphoric, nitric, ascorbic, methanesulfonic, acetic, propionic, tartaric, citric, lactic, malic, mandelic, cinnamic, palmitic, itaconic, fumaric, benzenesulfonic and toluenesulfonic. The non-toxic, physiologically acceptable salts are preferred, although other salts are also useful, for example, in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed $in\ vacuo$ or by freeze-drying, or by exchanging the cations of an existing salt for another cation on a suitable ion exchange resin.

The ability of the oxazolone derivatives of this invention to reverse drug resistance in multi-drug resistant tumors can be demonstrated by the ability of test compounds to reduce cell growth in a vinblastine (VBL) resistant tumor cell line.

$CHO^R$ cells were plated at a density of $1 \times 10^5/35$ mm dish and were allowed to grow overnight at 37° C. in a $CO_2$ incubator. The medium was replaced with medium containing the compounds and vinblastine (0.2 μg/ml). The cells were allowed to grow for further 72 hr and the cell number was determined by Coulter counter after trypsinization. VLB alone at 0.2 μg/ml did not have any effect on cell growth. the results of such a study employing 4-propyl-5-(4-pyridinyl)-2(3H)-oxazolone is tabulated in Table 1.

TABLE 1

REVERSAL OF MULTIDRUG RESISTANCE (MDR) IN $CHO^R$ CELLS BY 4-PROPYL-5-(4-PYRIDINYL)-2(3H)-OXAZOLONE

| Concentration (μg/ml) | % Inhibition of Cell Growth | |
|---|---|---|
| | Compound Only | Compound + VLB |
| 10 | 55 | 82 |
| 1 | 0 | 22 |
| 0.1 | 0 | 6 |

The term "patient" used herein is taken to mean mammals such as primates, including humans, sheep, horses, cattle, pigs, dogs, cats, rats and mice.

The amount of the oxazolone derivative of formula 1 to be administered can vary widely according to the particular dosage unit employed, the period of treatment, the age and sex of the patient treated, the nature and extent of the drug resistance in the tumor to be treated, and the particular oxazolone derivative selected. The oxazolone derivative is used in conjunction with other chemotherapeutic agents known to be useful in the treatment of tumors. The amount of a oxazolone derivative of formula 1 effective to reverse drug resistance will generally range from about 15 mg/kg to 500 mg/kg. A unit dosage may contain from 25 to 500 mg of the oxazolone derivative, and can be taken one or more times per day. The oxazolone derivative can be administered with a pharmaceutical carrier using conventional dosage unit forms either orally or parenterally.

Treatment of tumors by the method of this invention requires that an anti-tumor effective amount of a chemotherapeutic agent be administered together with a compound of formula 1. Tumors which can be treated by the method of this invention include both benign and malignant tumors or neoplasms, and include melanomas, lymphomas, leukemias, and sarcomas. Illustrative examples of tumors are cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseus or non-osseus sarcomas, breast tumors; tumors of the pituitary, thyroid and adrenal cortex; gastrointestinal tumors, such as those of the esophagus, stomach, intestine and colon; pancreatic and hepatic tumors; laryngeae papillomestasas and lung tumors. Of course those tumors which typically are or become multi-drug resistant are most beneficially treated with the method of this invention. Such tumors include colon tumors, lung tumors, stomach tumors, and liver tumors.

The effective amount of chemotherapeutic agent used in the method of this invention varies widely and depends on factors such as the patient, the tumor tissue type and its size, and the particular chemotherapeutic agent selected. The amount is any effective amount and can be readily determined by those skilled in the art. In general, less chemotherpeutic agent will be required when administered with the oxazolones of formula 1, primarily because the problem of drug resistance need not addressed by the addition of larger quantities of chemotherapeutic agent. Of course mixtures of chemotherapeutic agents may be employed and surgical excission and radiation therapy may be useful adjuvents as in any tumor therapy. While the compound of formula 1 and the chemotherapeutic agent are said to be administered together, this does not necessarily mean that the compounds are formulated into the same dosage form or are administered concurrently. Rather, the expression "together" means that a compound of formula 1 and the chemotherapeutic agent(s) are administered in a combined dosage form or separately during the course of therapy.

The preferred route of administration is oral administration. For oral administration the oxazolone derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The oxazolone derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The following specific examples are presented to illustrate the synthesis of the compounds of this invention, but they should not be construed as limiting the scope of this invention in any way.

EXAMPLE 1

4-Ethyl-5-Pyridin-4-yl-2(3H)-Ozazolone

1-Hydroxy-2-(4-pyridyl)butan-2-one (26.4 g, 0.16 mol) was dissolved in 350 ml of 2N HCl. Potassium cyanate (38.9 g, 0.48 mol) was added portionwise to this solution over a period of one hour with stirring. After the addition was complete, concentrated hydrochloric acid was added until the pH of the solution was one. After an additional hour the reaction mixture was made basic by addition of sodium bicarbonate solution and the resulting mixture was stirred overnight. The resulting solid precipitate was collected and recrystallized twice from 50% aqueous ethanol to yield the title compound (14.4 g, 47% of theoretical yield), m.p. 287°–289° C. (dec.).

Using the procedure above but using 1-(hydroxy)-1-(4-pyridyl)pentan-2-one or 1-(hydroxy)-1-(4-pyridyl)-propan-2-one instead of 1-hydroxy-1-(4-pyridyl)butan-2-one results in 4-propyl-5-pyridin-4-2 (3H)-oxazolone, m.p. 257°–259° C. (dec.) or 4-methyl-5-pyridin-4-yl-2(3H)-oxazolone, m.p. >310° C.

EXAMPLE 2

4-Ethyl-5-(2-pyridyl)-2(3H)-oxazolone

Potassium cyanate (35.4 g, 0.44 mol) was added to a solution of 2-hydroxy-1-(2-pyridyl)butan-1-one (31 g, 0.15 mol) in 250 ml of 2N HCl diluted with 300 ml of water. After 1 hour the acidity was adjusted (pH=1) with concentrated hydrochloric acid and then allowed to stir overnight. The mixture was made basic by addition of aqueous sodium bicarbonate. The resulting gummy precipitate was chromatographed on silca gel and recrystallized twice from 50% aqueous ethanol to give the title compound, m.p. 196°–197° C. (dec.).

In a manner substantially similar to that of Examples 1 and 2, the compounds 4-phenyl-5-pyridin-4-yl-2(3H)oxazolone (mp >300° C.) and 4-propyl-5-(2-phenylpyridin-4-yl)-2(3H)-oxazolone (mp 202°–204° C.) were prepared.

EXAMPLE 3

A tablet is prepared from

| | |
|---|---|
| 4-propyl-5-pyridin-4-yl-2(3H)-oxazolone | 250 mg |
| starch | 40 mg |
| talc | 10 mg |
| magnesium stearate | 10 mg |

EXAMPLE 4

A capsule is prepared from

| | |
|---|---|
| 4-ethyl-5-pyridin-4-yl-2(3H)-oxazolone | 400 mg |
| talc | 40 mg |
| sodium carboxymethylcellulose | 40 mg |
| starch | 120 mg |

EXAMPLE 5

A tablet is prepared from

| | |
|---|---|
| 4-Methyl-5-(3-pyridinyl)-1-(3H)-oxazolone | 250 mg |
| Starch | 40 mg |
| Talc | 10 mg |
| Magnesium | 10 mg |

EXAMPLE 6

A capsule is prepared from

| | |
|---|---|
| 4-phenyl-5-(2-pyridinyl)1-(3H)-oxazolone | 400 mg |

| | |
|---|---|
| Talc | 40 mg |
| Sodium Carboxymethyl cellulose | 40 mg |
| Starch | 120 mg |

It should be apparent to one of ordinary skill in the art that changes and modifications can be made to this invention without departing from the spirit or scope of the invention as it is set forth herein.

What is claimed is:

1. A method of reversing vinblastine resistance in a patient having a vinblastine resistant tumor which comprises administering to said patient as effective amount of a compound of the formula:

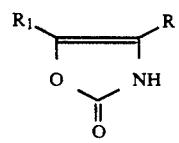

wherein
R is $C_{1-6}$ alkyl; and
$R_1$ is 2-, 3- or 4-pyridyl group; or a pharmaceutically acceptable salt thereof.

* * * * *